United States Patent [19]

Sabol et al.

[11] 4,113,634

[45] Sep. 12, 1978

[54] METAL ARYL DITHIOPHOSPHATES AND THEIR MANUFACTURE

[75] Inventors: Albert R. Sabol, Munster, Ind.; Nicolas C. Petrellis, Lisle, Ill.

[73] Assignee: Standard Oil Company (Indiana), Chicago, Ill.

[21] Appl. No.: 773,346

[22] Filed: Mar. 1, 1977

[51] Int. Cl.$^2$ .............. C10M 1/48; C10M 3/42; C10M 5/24; C10M 7/46

[52] U.S. Cl. .............. 252/32.7 E; 252/389 A; 252/400 A

[58] Field of Search .............. 252/32.5, 32.7 E, 389 A, 252/400 A

[56] References Cited

U.S. PATENT DOCUMENTS 3,086,939  4/1963  Tichelaar et al. .............. 252/32.7 E
3,290,347  12/1966  Miller .............. 252/32.7 E Primary Examiner—Irving Vaughn
Attorney, Agent, or Firm—Frank J. Sroka; Arthur G. Gilkes; William T. McClain

[57] ABSTRACT

Disclosed are a process for manufacturing metal diaryl dithiophosphates, certain metal diaryl dithiophosphates, and lubricating oil compositions containing said metal diaryl dithiophosphates. The process for the manufacture of metal diaryl dithiophosphate generally comprises reacting $P_2S_5$ with a hydroxyl aryl compound to form a dithiophosphoric acid; and neutralizing said dithiophosphoric acid with zinc, barium, cadmium, magnesium or nickel base in the presence of an effective amount of a promoter, said promoter comprising dialkyl dithiophosphoric acid. Metal diaryl dithiophosphates, especially for use in lubricating oil compositions, can be made by the above process.

31 Claims, No Drawings

METAL ARYL DITHIOPHOSPHATES AND THEIR MANUFACTURE

BACKGROUND

This invention relates to additive compositions, lubricating oil compositions containing said additive compositions, and a process for manufacturing said additive compositions. More specifically, it relates to metal diaryl dithiophosphates and their manufacture and use.

It is well known that various additives can be added to lubricating oils in order to improve various oil properties and to make a lubricant. satisfactory lubricate. Antiwear agents are intended to decrease wear of machine parts. Wear inhibitors for incorporation in motor oils and industrial oils are finding greater use as a result of greater stress placed on moving parts in high performance engines. Numerous additives have been developed for use in such oil compositions to improve the lubricating characteristics thereof and thereby to lessen the wear of the moving parts.

Metal diaryl dithiophosphates, especially zinc diaryl dithiophosphates, have long been used as antiwear additives and antioxidants in hydraulic oils, motor oils and automatic transmission fluids. In the manufacture of such metal diaryl dithiophosphates, an aryl dithiophosphoric acid is commonly neutralized with a base, such as zinc oxide or hydroxide. This neutralization step does not take place readily and commonly a large excess of the base is used in conjunction with a neutralization promoter and high neutralization temperatures. Sometimes the use of promoters such as nitric acid can lead to undesirable side effects. In many cases the neutralized product is difficult to filter and has a dark color. The effectiveness of a compound as a neutralization promoter is difficult to predict and therefore such promoters are generally determined on an empirical basis.

It is an object of this invention to provide an improved process for the manufacture of metal diaryl dithiophosphates.

It is an object of this invention to provide a process for the manufacture of metal diaryl dithiophosphates wherein less excess metal base is required for the neutralization of dithiophosphoric acids.

It is an object of this invention to provide a process for the manufacture of metal diaryl dithiophosphates using lower neutralization temperature or shorter neutralization time.

It is an object of this invention to provide a process for the manufacture of metal diaryl dithiophosphates wherein the neutralized product has a light color and high filtration rates.

It is further an object of this invention to provide a highly effective antiwear and antioxidant additive for use in lubricating oils.

SUMMARY OF THE INVENTION

Disclosed are metal diaryl dithiophosphate compositions, lubricating oil compositions containing such diaryl dithiophosphates, and a process for manufacturing such diaryl dithiophosphates.

The process for the manufacture of metal diaryl dithiophosphate comprises reacting $P_2S_5$ with a hydroxyl aryl compound to form a dithiophosphoric acid; and neutralizing said dithiophosphoric acid with metal base such as zinc, barium, cadmium, magnesium or nickel base, in the presence of an effective amount of a promoter, said promoter comprising dialkyl dithiophosphoric acid.

Preferably the promoter is present at a concentration of about 0.01 to about 1.0 moles per mole of aryl dithiophosphoric acid, more preferably about 0.11 to about 0.22 moles per mole of aryl dithiophosphoric acid. Preferred metal bases are zinc oxide or zinc hydroxide. Commonly $P_2S_5$ is reacted with the hydroxyl aryl compound at a temperature from about 100° to about 250° F and the neutralization with metal base is conducted at from about 100° to about 400° F.

The aryl dithiophosphates are manufactured from hydroxyl aryl compounds. These hydroxyl aryl compounds generally contain one, two or three aromatic rings but most commonly contain a single aromatic ring. Said hydroxyl aryl compounds may contain more than one hydroxy group but most commonly contain a single hydroxy group. The aromatic ring or rings may contain various other substitutions such as hydrocarbyl, chlorine, bromine, nitro and others. In some cases these substitutions do not enhance or detract from the effectiveness of the additive. In no case should the substitution interfere with the reaction with $P_2S_5$ or the neutralization step.

Commonly, hydrocarbyl substitution of the hydroxy aryl compound is desirable in order to improve the oil solubility and effectiveness of neutralized metal dithiophosphates as lubricating oil additives. Therefore, hydrocarbyl substituted hydroxy aryl compounds, such as hydrocarbyl phenols, are preferred.

The most commonly used substituted phenols contain one or more hydrocarbyl groups having about one to about 100 carbon atoms. Preferably, the hydrocarbyl groups contain about 8 to about 20 carbon atoms. The hydrocarbyl groups can be alkyl, alkenyl, aryl, aralkyl or alkaryl. Mono alkyl substitution is preferred. The hydrocarbon substitution can range from low molecular weight groups such as methyl, ethyl, propyl, isopropyl, butyl, isobutyl, and the like up to low molecular weight polymers and copolymers. Many commercially available substituted phenols contain $C_8$-$C_{20}$ substituents from polypropylene or polybutene. The hydrocarbyl substituted phenol may have other substituents, such as for example, chlorine, bromine, nitro or sulfonic acid groups.

The alkyl dithiophosphates are manufactured from hydroxy alkyl compounds such as alcohols. Metal dialkyl dithiophosphates are most commonly formed by the reaction of phosphorous pentasulfide with aliphatic alcohols to form phosphoric acid esters. The alcohols, often a mixture of alcohols, commonly contain from about 3 to about 20 carbon atoms, but preferably about 3 to about 12 carbon atoms. Sometimes dialkyl dithiophosphoric acids are represented as follows:

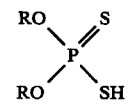

wherein R comprises an alkyl group containing about three to about twenty carbon atoms. These alkyl groups generally originate from alcohols such as propyl, n-butyl, n-pentyl, n-hexyl, n-heptyl, n-octyl, n-decyl, n-dodecyl, hexadecyl, octadecyl or branched chain alcohols such as the methyl or ethyl branched isomers of the above. Suitable branched alcohols are isopropyl, 2-methyl-1-1-pentanol, 2-ethyl-1-hexanol, 2,2-dimethyl-1- octanol, and alcohols prepared from olefin oligomers such as propylene dimer or trimer by hydroboration-oxidation or by the Oxo process. It may be preferable to use mixtures of alcohols because of their low cost and possible improvement in performance.

The dialkyl or diaryl dithiophosphoric acids are generally made by reaction of about 4 moles of hydroxy compound with one mole of a phosphorous pentasulfide containing about 27 weight percent phosphorus. The phosphosulfurizing agent used is phorphorus pentasulfide. The quality of the phosphorus pentasulfide is of some importance and this reagent should have approximately the following properties:

| | |
|---|---|
| Melting point, ° F. | 270–280 |
| Wt. percent phosphorus | 25–30 |
| Wt percent sulfur | 70–75 |
| Free of organic material. | |

The reaction is preferably but not necessarily conducted in a glass-lined vessel fitted with suitable agitation equipment. Commonly, the reaction is conducted at a temperature from about 100° to about 250° F for a period in the range of about 1–6 hours. The alcohol is preferably free of water.

A convenient method for controlling the end point of the reaction is to measure the specific gravity of the reaction product. The specific gravity will, of course, vary with the reaction temperature and with the excess alcohol content. The end point can also be determined by noting when the evolution of $H_2S$ ceases.

The diaryl dithiophosphoric acids are then reacted with a metal base such as zinc oxide or zinc hydroxide in order to form the metal diaryl dithiophosphate generally having a metal to phosphorus ratio of about 1–1.5:1. The neutralization reaction is usually carried out at elevated temperatures, e.g. temperatures in the range of about 100° to about 300°–400° F. Because the use of this neutralization promoter reduces the temperature required for neutralization, said neutralization can be conducted at a more convenient temperature of about 100° F to about 140° F. The neutralization is effected, for example, by contacting a zinc oxide slurry with diaryl dithiophosphoric acid for a time sufficient to neutralize the acid and possibly also incorporate an excess of zinc oxide so that the material is basic. The neutralization of the aryl dithiophosphoric acids is conducted in the presence of an effective amount of a neutralization promoter comprising alkyl dithiophosphoric acid. The promoter may be introduced into the neutralization reaction by being mixed with the aryl dithiophosphoric acid prior to or after the addition of metal base. The promoter may also be added separately. One preferred method of introducing the alkyl dithiophosphoric acid is by reacting the proper amount of alkyl alcohol with $P_2S_5$ along with the aryl alcohol when making the dithiophosphoric acid. In this case, the aryl dithiophosphoric acid will contain a small amount of alkyl dithiophosphoric acid. The neutralization reaction may usually be completed within a period of from about 10 minutes to about 4–5 hours. The neutralized product can be used as a corrosion inhibitor without the separation of oil slurry medium or, if a high-purity zinc dihydrocarbon dithiophosphate is desired, the oil medium may be separated from the salt by solvent extraction, distillation, etc.

Metal diaryl dithiophosphates can be prepared by batch or continuous processes. In batch processes, for example, a slurry of zinc oxide in oil is charged to a reaction zone containing dihydrocarbon dithiophosphoric acid and the acid is neutralized by the zinc oxide at elevated temperatures. In continuous processing, the slurry of zinc oxide and the dihydrocarbon dithiophosphoric acid may be charged to one end of a reaction zone, e.g. the upper end of a vertical zone, maintained at elevated temperatures and the product neutralized zinc dihydrocarbon dithiophosphate may be withdrawn from the other end of the reaction zone. If desired, the product from either the batch or continuous process may be further purified by clay percolation or the like to remove insoluble components.

The oil used in the slurry is preferably a light lubricating oil; however, heavier lubricating oils can be used if desired. The lighter oils are preferred because of their lower viscosities and the greater ease of pumping such oils or slurries containing such oils. Although hydrocarbon oils and particularly petroleum oils were utilized in the procedure set out below, it is intended that other oils can also be used such as the synthetic hydrocarbon polymer oils prepared by the condensation and other methods. Ester oils are not preferred because of the possibility of their dissociation in the presence of zinc oxide under the neutralization reaction conditions. Other useable oils are the distillate fuel oils such as kerosene, heater oils, dewaxed cycle oils and the like. The light lubricating oils are particularly preferred.

One means of introducing the $P_2S_5$ into the reaction vessel is by slurrying the dry $P_2S_5$ with the alcohol or alcohols that are to be used in the process to form the dialkyl-oxy radicals of the dithiophosphoric acid. The slurry is preferably kept cold enough to minimize reaction of the $P_2S_5$, and alcohol prior to introduction into the reaction vessel. Sometimes it is also suitable to slurry the base, such as ZnO or $Zn(OH)_2$, in the same alcohol in order to transport it to the reactor.

The lubricating oils in which the compositions of this invention are useful as additives and which comprise a major proportion of the lubricating oil compositions may be of synthetic, animal, vegetable, or mineral origin. Ordinarily mineral lubricating oils are preferred by reason of their availability, general excellence, and low cost. For certain applications, oils belonging to one of the other three groups may be preferred. For instance, synthetic polyester oils such as didodecyl adipate and di-2-ethylhexyl sebacate are often preferred as jet engine lubricants. Normally the lubricating oils preferred will be fluid oils, ranging in viscosity from about 40 Saybolt Universal seconds at 100° to about 200 Saybolt Universal seconds at 210° F. This invention contemplates also the presence of other additives in lubricating compositions. Such additives include, for example, viscosity index improving agents, pour point depressing agents, anti-foam agents, extreme pressure agents, rust-inhibiting agents, and oxidation and corrosion inhibiting agents.

The additive of this invention is generally added to lubricating oil in order to improve the antiwear or antioxidant properties of said oil. Depending on the nature of the oil, the intended use and the desired improvement, different amounts of the additive are needed in order to be effective. Generally about 0.05 to about 5 weight percent, preferably from about 0.1 to about 2 weight percent, of the additive is used.

Zinc diaryl dithiophosphates were made by different neutralization processes.

EXAMPLE I

Diaryl dithiophosphoric acid was reacted with zinc oxide without a promoter.

The aryl dithiophosphoric acid for the examples was made by adding 762 grams (3.4 moles) of $P_2S_5$ and 668 grams of 5 w oil to a reactor and heating to 160° F. 2988 grams (13.6 moles) of nonyl ($C_9$ polybutene) mono substituted phenol was added and the mixture heated to 200° F. The reaction is exothermic. The mixture is heated or allowed to rise to 220° F and held at that temperature for one hour. The mixture is then heated to 250° F and held at that temperature for one hour. The mixture is then blown with nitrogen for 15 minutes, cooled to 180° F and filtered. The product aryl dithiophosphoric acid contains 4.03 percent phosphorus and 8.05 percent sulfur.

81 grams of zinc oxide were slurried in 403 cc 5 w oil and charged to a reactor. The slurry was heated to 110°-120° F and 1000 grams of di-nonylphenol-dithiophosphoric acid was added, maintaining the temperature below 170° F. After one-half hour, the mixture was sour when tested with lead acetate paper. The mixture was heated to 210°-220° F and after one hour the mixture was still sour.

EXAMPLE 2

Diaryl dithiophosphoric acid was neutralized with zinc oxide in the presence of nitric acid promoter.

81 grams zinc oxide were slurried in 403 cc 5 w oil and added to a reactor. The slurry was heated to 110°-120° F and 100 grams of dinonylphenol dithiophosphoric acid was added while maintaining the temperature below 170° F. After addition of the phosphoric acid, 2 cc of $HNO_3$ were added. The mixture became sweet in 4 minutes. The mixture was then heated to 210°-220° F. for one hour to remove water and then filtered. It should be noted that a 50 percent excess of zinc oxide was used. The product contained 2.7 percent phosphorus and 3.1 percent zinc.

EXAMPLE 3

Diaryl dithiophosphoric acid was neutralized in the presence of dialkyl dithiophosphoric acid.

To a slurry of 345 grams of 5 w oil and 81 grams zinc oxide at 110° F, a mixture of 1000 grams (1.36 moles) of di-nonylphenol dithiophosphoric acid and 100 grams (0.3 moles) of dialkyl dithiophosphoric acid made from a mixture of $C_3$-$C_8$ alcohols was slowly added, maintaining the temperature at about 130°-140° F. After addition was completed, the temperature was allowed to increase to about 150° F. The product became sweet within three minutes of contact with the metal base. The product was heated to 200° F with nitrogen blowing and maintained at 200° F for 30 minutes to remove water of neutralization. The product was then filtered through a celite pad.

The dialkyl dithiophosphoric acid used as a neutralization promoter was made by reacting one mole $P_2S_5$ per four moles of a mixture of aliphatic $C_3$-$C_8$ alcohols. 222 grams of $P_2S_5$ and 90 grams 5 w oil were charged to a reactor. The slurry was heated to 110°-120° F and 332 grams of a mixture of alcohols was added. The temperature was maintained below 200° F during addition. The $P_2S_5$-alcohol reaction was conducted at 200°-210° F for 1.5 hours. The reaction mixture was then blown with nitrogen for 15 minutes, cooled to 170° F and filtered.

The product contained 9.36 percent phosphorus and 19.7 percent sulfur.

We claim:

1. A process for the manufacture of metal diaryl dithiophosphate which comprises:
   reacting $P_2S_5$ with a hydroxyl aryl compound to form a dithiophosphoric acid; and
   neutralizing said dithiophosphoric acid with zinc, barium, cadmium, magnesium or nickel base in the presence of an effective amount of a promoter, said promoter comprising dialkyl dithiophosphoric acid.

2. The process of claim 1 wherein the promoter is present at a concentration of about 0.01 to about 1.0 moles per mole of aryl dithiophosphoric acid.

3. The process of claim 1 wherein the promoter is present at a concentration of about 0.11 to about 0.22 moles per mole of aryl dithiophosphoric acid.

4. The process of claim 1 wherein the dithiophosphoric acid is neutralized with a zinc base.

5. The process of claim 4 wherein the zinc base comprises zinc oxide or zinc hydroxide.

6. The process of claim 4 wherein the promoter comprises a $C_3$ to $C_8$ dialkyl dithiophosphate.

7. The process of claim 1 wherein said hydroxy aryl compound comprises a hydroxy substituted benzene ring.

8. The process of claim 7 wherein said benzene ring is substituted with a $C_1$ to $C_{100}$ hydrocarbyl group.

9. The process of claim 1 wherein the reaction of $P_2S_5$ with the hydroxy aryl compound is conducted at a temperature of from about 100° to about 250° F and the neutralization of said aryl dithiophosphoric acid is conducted at a temperature of from about 100° to about 400° F.

10. A process for the manufacture of zinc diaryl dithiophosphate which comprises:
    reacting $P_2S_5$ with a hydroxy substituted benzene compound to form a diaryldithiophosphoric acid at a temperature from about 100° to about 250° F; and
    neutralizing said diaryldithiophosphoric acid with zinc oxide or zinc hydroxide in the presence of about 0.11 to about 0.22 moles of a promoter per mole of aryl dithiophosphoric acid at a temperature from about 100° to about 400° F, said promoter comprising $C_3$ to $C_8$ dialkyl dithiophosphoric acid.

11. A metal diaryl dithiophosphate made by a process which comprises:
    reacting $P_2S_5$ with a hydroxy aryl compound to form a dithiophosphoric acid; and
    neutralizing said dithiophosphoric acid with zinc, barium, cadmium, magnesium or nickel base in the presence of small amounts of a promoter, said promoter comprising dialkyl dithiophosphoric acid.

12. The diaryl dithiophosphate of claim 11 wherein the promoter is present at a concentration of about 0.01 to about 1.0 moles per mole of aryl dithiophoshoric acid.

13. The diaryl dithiophosphate of claim 11 wherein the promoter is present at a concentration of about 0.11 to about 0.22 moles per mole of aryl dithiophosphoric acid.

14. The diaryl dithiophosphate of claim 11 wherein the dithiophosphoric acid is neutralized with a zinc base.

15. The diaryl dithiophosphate of claim 14 wherein the zinc base comprises zinc oxide or zinc hydroxide.

16. The diaryl dithiophosphate of claim 14 wherein the promoter comprises a $C_3$ to $C_8$ dialkyl dithiophosphate.

17. The diaryl dithiophosphate of claim 11 wherein said hydroxy aryl compound comprises a hydroxy substituted benzene ring.

18. The diaryl dithiophosphate of claim 17 wherein said benzene ring is substituted with a $C_1$ to $C_{100}$ hydrocarbyl group.

19. The diaryl dithiophosphate of claim 11 wherein the reaction of $P_2S_5$ with the hydroxy aryl compound is conducted at a temperature of from about 100° to about 250° F and the neutralization of said aryl dithiophosphoric acid is conducted at a temperature of from about 100° to about 400° F.

20. A zinc diaryl dithiophosphate made by a process which comprises:
  reacting $P_2S_5$ with a hydroxy substituted benzene compound to form a diaryldithiophosphoric acid at a temperature from about 100° to about 250° F; and
  neutralizing said diaryldithiophoshoric acid with zinc oxide or zinc hydroxide in the presence of about 0.11 to about 0.22 moles of a promoter per mole of aryl dithiophosphoric acid at a temperature from about 100° to about 400° F, said promoter comprising $C_3$ to $C_8$ dialkyl dithiophosphoric acid.

21. A lubricating oil composition comprising a major proportion of lubricating oil and about 0.05 to about 5 weight percent of a metal diaryl dithiophosphate, said diaryl dithiophosphate made by a process comprising:
  reacting $P_2S_5$ with a hydroxy aryl compound to form a dithiophosphoric acid; and
  neutralizing said dithiophosphoric acid with zinc, barium, cadmium, magnesium or nickel base in the presence of small amounts of a promoter, said promoter comprising dialkyl dithiophosphoric acid.

22. The composition of claim 21 wherein the promoter is present at a concentration of about 0.01 to about 1.0 moles per mole of aryl dithiophosphoric acid.

23. The composition of claim 21 wherein the promoter is present at a concentration of about 0.11 to about 0.22 moles per mole of aryl dithophosphoric acid.

24. The composition of claim 21 wherein the dithiophosphoric acid is neutralized with a zinc base.

25. The composition of claim 24 wherein the zinc base comprises zinc oxide or zinc hydroxide.

26. The composition of claim 24 wherein the promoter comprises a $C_3$ to $C_8$ dialkyl dithiophosphate.

27. The composition of claim 21 wherein said hydroxy aryl compound comprises a hydroxy substituted benzene ring.

28. The composition of claim 22 wherein said benzene ring is substituted with a $C_1$ to $C_{100}$ hydrocarbyl group.

29. The composition of claim 21 wherein the reaction of $P_2S_5$ with the hydroxy aryl compound is conducted at a temperature of from about 100° to about 250° F and the neutralization of said aryl dithiophosphoric acid is conducted at a temperature of from about 100° to about 400° F.

30. A lubricating oil composition comprising a major proportion of lubricating oil and about 0.05 to about 5 weight percent of a zinc diaryl dithiophosphate, said diaryl dithiophosphate made by a process comprising:
  reacting $P_2S_5$ with a hydroxy substituted benzene compound to form a diaryldithiophoshoric acid at a temperature from about 100° to about 250° F; and
  neutralizing said diaryldithiophosphoric acid with zinc oxide or zinc hydroxide in the presence of about 0.11 to about 0.22 moles of a promoter per mole of aryl dithiophosphoric acid at a temperature from about 100° to about 400° F, said promoter comprising $C_3$ to $C_8$ dialkyl dithiophosphoric acid.

31. The composition of claim 21 wherein the lubricating oil has a viscosity from about 40 Saybolt Universal Seconds at 100° F to about 200 Saybolt Universal Seconds at 210° F.

* * * * *